Pending>

(12) United States Patent
Bonda et al.

(10) Patent No.: US 9,443,624 B2
(45) Date of Patent: Sep. 13, 2016

(54) ARYL SUBSTITUTED PROPENOIC AMIDES AND ESTERS

(71) Applicant: HALLSTAR INNOVATIONS CORP., Chicago, IL (US)

(72) Inventors: Craig Bonda, Winfield, IL (US); Shengkui Hu, Darien, IL (US); Gary A. Neudahl, Cary, IL (US); Stephen O'Rourke, Bolingbrook, IL (US); Stephen J. Semlow, Chicago, IL (US); Zhihui Zhang, Downers Grove, IL (US)

(73) Assignee: HALLSTAR INNOVATIONS CORP., Chicago, IL (US)

( * ) Notice: Subject to any disclaimer, the term of this patent is extended or adjusted under 35 U.S.C. 154(b) by 0 days.

(21) Appl. No.: 14/452,356

(22) Filed: Aug. 5, 2014

(65) Prior Publication Data

US 2015/0044149 A1 Feb. 12, 2015

Related U.S. Application Data

(60) Provisional application No. 61/862,900, filed on Aug. 6, 2013.

(51) Int. Cl.
| | |
|---|---|
| *G21F 1/10* | (2006.01) |
| *C07C 327/12* | (2006.01) |
| *C07C 255/41* | (2006.01) |
| *A61Q 17/04* | (2006.01) |
| *A61K 31/277* | (2006.01) |
| *A61K 8/46* | (2006.01) |
| *A61K 8/42* | (2006.01) |

(52) U.S. Cl.
CPC . *G21F 1/10* (2013.01); *A61K 8/42* (2013.01); *A61K 8/46* (2013.01); *A61K 31/277* (2013.01); *A61Q 17/04* (2013.01); *C07C 255/41* (2013.01); *C07C 327/12* (2013.01)

(58) Field of Classification Search
CPC .. A61K 8/42; A61K 31/277; A61K 2800/10; C07C 237/12; C07C 255/41; G21F 1/10; A61Q 17/04
See application file for complete search history.

(56) References Cited

U.S. PATENT DOCUMENTS

| | | | | |
|---|---|---|---|---|
| 4,883,653 A * | 11/1989 | Raynor | ............... | A61K 8/42 424/60 |
| 5,888,481 A * | 3/1999 | Horn | ............... | C07C 255/41 424/59 |
| 6,627,180 B2 * | 9/2003 | Candau | ............... | A61K 8/0241 424/59 |
| 7,276,230 B2 * | 10/2007 | Gonzalez | ............... | A61K 8/40 424/59 |
| 7,799,317 B2 * | 9/2010 | Bonda | ............... | A61K 8/85 424/59 |
| 7,964,245 B2 * | 6/2011 | Bonda | ............... | C08F 222/06 427/385.5 |

FOREIGN PATENT DOCUMENTS

JP 61192780 * 8/1986 ............... C09K 3/00

* cited by examiner

*Primary Examiner* — Jane C Oswecki
(74) *Attorney, Agent, or Firm* — Baker & McKenzie LLP

(57) ABSTRACT

The present disclosure relates, according to some embodiments, to molecules, including substituted propenoic amides (e.g., aryl substituted propenoic amides), that may receive excited state energy from light-absorbing molecules. According to some embodiments, the present disclosure relates to molecules, including substituted propenoic amides (e.g., aryl substituted propenoic amides), that may quench, dissipate, and/or otherwise resolve excited state energy (e.g., as heat).

20 Claims, No Drawings

ARYL SUBSTITUTED PROPENOIC AMIDES AND ESTERS

CROSS-REFERENCE TO RELATED APPLICATIONS

This application claims priority to U.S. Provisional Application No. 61/862,900 filed Aug. 6, 2013 entitled "Aryl substituted propenoic amides and esters," the contents of which are hereby incorporated in their entirety by reference.

FIELD OF THE DISCLOSURE

The present disclosure relates, in some embodiments, to molecules, including substituted propenoic amides and thiol esters, that may receive energy from other light-absorbing molecules or directly from the irradiation sources. According to some embodiments, the present disclosure relates to molecules, including substituted propenoic amides and thiol esters, that may quench, dissipate, and/or otherwise resolve excited state energy (e.g., releasing it as heat).

BACKGROUND OF THE DISCLOSURE

Irradiation energy can have a detrimental impact on exposed substances and organisms. When a molecule absorbs light, the absorbed photon may propel an electron from a lower energy orbital (e.g., ground state) to a higher energy orbital (e.g., excited state). A molecule with an excited electron may be unstable; it may readily react with surrounding molecules to release the excited state energy and return its electron to a lower energy state. The manner in which the excited energy state is resolved may have a substantial impact on the ultimate effect of the absorption event. For example, photosynthetic organisms can harvest the absorbed energy and convert it to usable chemical energy. In many cases, however, excited state energy is resolved in less productive and even detrimental ways. For example, reactive oxygen species and other reactive free radicals may be formed. These highly reactive species often react by oxidizing one or more surrounding molecules. The resulting damage may vary in kind and extent. Other consequences of reactions resulting from excited state molecules may include: bleaching pigment molecules, degrading polymers, mutating DNA, damaging plasma membranes, and/or activing intracellular signaling ectopically and/or deleteriously.

SUMMARY

Accordingly, a need has arisen for improved compositions, methods, and systems for dissipating, quenching or otherwise resolving excited energy states (e.g., light-induced excited energy states) with fewer adverse effects.

The present disclosure relates, according to some embodiments, to molecules, including substituted propenoic amides and thiol esters (e.g., aryl substituted propenoic amides and thiol esters), that may receive excited state energy from light-absorbing molecules or directly from the irradiation sources. According to some embodiments, the present disclosure relates to molecules, including substituted propenoic amides and thiol esters (e.g., aryl substituted propenoic amides and thiol esters), that may quench, dissipate, and/or otherwise resolve excited state energy (e.g., releasing it as heat).

The present disclosure relates, according to some embodiments, to substituted propenoic amide molecules and compositions that may comprise a photoactive molecule and a substituted propenoic amide. A substituted propenoic amide may have, for example, a structure according to Formula I:

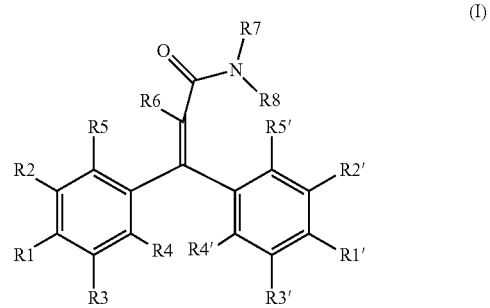

In some embodiments, R1 and R1' may each, independently, comprise a methoxyl group (—OCH$_3$) or a hydrogen (H) with at least one being a methoxyl group (—OCH$_3$). In some embodiments, R2, R2', R3, R3', R4, R4', R5, R5' may each, independently, comprise H, OH, alkyl, alkoxyl, or a substituted alkyl group. In some embodiments, R6 may comprise cyano or

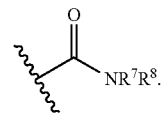

In some embodiments, R7 and R8 may each, independently, comprise H, alkyl, substituted alkyl or a polymeric structure. In some embodiments, the aryl substituted propenoic amide may be configured (a) to resolve at least one excited state of the photoactive molecule substantially without observable (e.g., detectable) photochemical reaction, (b) to resolve at least one excited state of the photoactive molecule substantially non-radiatively, or (c) to resolve at least one excited state of the photoactive molecule substantially without observable (e.g., detectable) photochemical reaction and substantially non-radiatively.

In a propenoic amide with a structure according to Formula I, R1 may be a hydrogen and R1' may be a methoxyl group (—OCH$_3$), according to some embodiments. In a propenoic amide with a structure according to Formula I, R1 may be a methoxyl group (—OCH$_3$) and R1' may be a hydrogen, according to some embodiments.

In a propenoic amide with a structure according to Formula I, at least one of R2, R2', R3, R3', R4, R4', R5, and R5' may be an alkyl group having from about 1 to about 30 carbon atoms, according to some embodiments. In a propenoic amide with a structure according to Formula I, at least one of R2, R2', R3, R3', R4, R4', R5, and R5' may be a substituted alkyl group, according to some embodiments.

In a propenoic amide with a structure according to Formula I, at least one of R2, R2', R3, R3', R4, R4', R5, and R5' may be an alkoxyl group, according to some embodiments.

In a propenoic amide with a structure according to Formula I, R6 may be

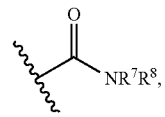

according to some embodiments.

The present disclosure relates, according to some embodiments, to a paint, a coating, a cosmetic, a sunscreen, or a pharmaceutical that may comprising a substituted propenic amide according to Formula I and/or a photoactive molecule.

The present disclosure relates, according to some embodiments, to methods for resolving at least one excited energy state of a photoactive molecule. In some embodiments, the method may comprise positioning the photoactive molecule in electrical communication with a substituted propenoic amide prior to, during, or following excitation of the photoactive molecule to the at least one excited energy state. A substituted propenoic amide for use in such a method may have a structure according to Formula I. In some embodiments, R1 and R1' may each, independently, comprise a methoxyl group (—OCH$_3$) or a hydrogen (H) with at least one being a methoxyl group (—OCH$_3$). In some embodiments, R2, R2', R3, R3', R4, R4', R5, R5' may each, independently, comprise H, OH, alkyl, alkoxyl, or a substituted alkyl group. In some embodiments, R6 may comprise cyano or

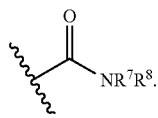

In some embodiments, R7 and R8 may each, independently, comprise H, alkyl, substituted alkyl or a polymeric structure.

According to some embodiments, the at least one excited state of the photoactive molecule may be resolved substantially without observable (e.g., detectable) photochemical reaction. According to some embodiments, the at least one excited state of the photoactive molecule may be resolved substantially non-radiatively. According to some embodiments, the at least one excited state of the photoactive molecule may be resolved substantially without observable (e.g., detectable) photochemical reaction and substantially non-radiatively.

The present disclosure relates, according to some embodiments, to substituted propenoic thiol ester molecules and compositions that may comprise a photoactive molecule and a substituted propenoic thiol ester. A substituted propenoic thiol ester may have, for example, a structure according to Formula II:

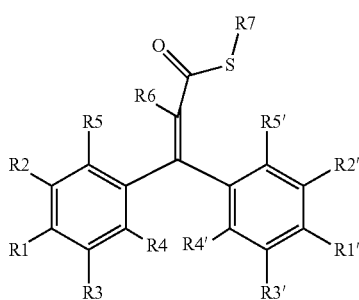

(II)

In some embodiments, R1 and R1' may each, independently, comprise a methoxyl group (—OCH$_3$) or a hydrogen (H) with at least one being a methoxyl group (—OCH$_3$). In some embodiments, R2, R2', R3, R3', R4, R4', R5, R5' may each, independently, comprise H, OH, alkyl, alkoxyl, or a substituted alkyl group. In some embodiments, R6 may comprise cyano or

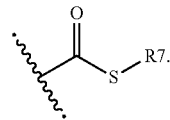

In some embodiments, R7 may be selected from alkyl, substituted alkyl or a polymeric structure. In some embodiments, the aryl substituted propenoic thiol ester may be configured (a) to resolve at least one excited state of the photoactive molecule substantially without observable (e.g., detectable) photochemical reaction, (b) to resolve at least one excited state of the photoactive molecule substantially non-radiatively, or (c) to resolve at least one excited state of the photoactive molecule substantially without observable (e.g., detectable) photochemical reaction and substantially non-radiatively.

In a propenoic thiol ester with a structure according to Formula II, R1 may be a hydrogen and R1' may be a methoxyl group (—OCH$_3$), according to some embodiments. In a propenoic thiol ester with a structure according to Formula II, R1 may be a methoxyl group (—OCH$_3$) and R1' may be a hydrogen, according to some embodiments.

In a propenoic thiol ester with a structure according to Formula II, at least one of R2, R2', R3, R3', R4, R4', R5, and R5' may be an alkyl group having from about 1 to about 30 carbon atoms, according to some embodiments. In a propenoic thiol ester with a structure according to Formula II, at least one of R2, R2', R3, R3', R4, R4', R5, and R5' may be a substituted alkyl group, according to some embodiments.

In a propenoic thiol ester with a structure according to Formula II, at least one of R2, R2', R3, R3', R4, R4', R5, and R5' may be an alkoxyl group, according to some embodiments.

In a propenoic thiol ester with a structure according to Formula II, R6 may be

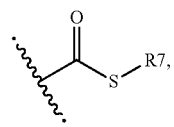

according to some embodiments.

The present disclosure relates, according to some embodiments, to a paint, a coating, a cosmetic, a sunscreen, or a pharmaceutical that may comprising a substituted propenic thiol ester according to Formula II and/or a photoactive molecule.

The present disclosure relates, according to some embodiments, to methods for resolving at least one excited energy state of a photoactive molecule. In some embodiments, the method may comprise positioning the photoactive molecule in electrical communication with a substituted propenoic thiol ester prior to, during, or following excitation of the photoactive molecule to the at least one excited energy state A substituted propenoic thiol ester for use in such a method may have a structure according to Formula II. In some embodiments, R1 and R1' may each, independently, comprise a methoxyl group (—OCH$_3$) or a hydrogen (H) with at least one being a methoxyl group (—OCH$_3$). In some embodiments, R2, R2', R3, R3', R4, R4', R5, R5' may each, independently, comprise H, OH, alkyl, alkoxyl, or a substituted alkyl group. In some embodiments, R6 may comprise cyano or

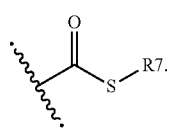

In some embodiments, R7 may be selected from alkyl, substituted alkyl or a polymeric structure.

According to some embodiments, the at least one excited state of the photoactive molecule may be resolved substantially without observable (e.g., detectable) photochemical reaction. According to some embodiments, the at least one excited state of the photoactive molecule may be resolved substantially non-radiatively. According to some embodiments, the at least one excited state of the photoactive molecule may be resolved substantially without observable (e.g., detectable) photochemical reaction and substantially non-radiatively.

DETAILED DESCRIPTION

The present disclosure relates, in some embodiments, to molecules that may receive excited state energy from other molecules (e.g., light-absorbing molecules). According to some embodiments, the present disclosure also relates to molecules that may quench, dissipate, and/or otherwise resolve excited state energy. A molecule that donates excited state energy may be referred to as a donor molecule and/or a molecule that receives excited state energy may be referred to as a receiver or acceptor molecule in some embodiments. An acceptor molecule may comprise, for example, an aryl substituted propenoic amide or thiol ester. In some embodiments, a donor molecule may be a photoactive—it may absorb incident radiation (e.g., UV radiation). For example, a molecule exposed to light may absorb one or more photons. Absorbed energy (e.g., photons) may raise a low energy state electron (e.g., ground state electron) to an excited energy state (e.g., singlet or triplet). Formation and/or resolution of the excited energy state may lead to unwanted effects including, for example, formation of radicals and/or chemical breakdown of polymers, dyes, and/or pigments.

Various strategies may be adopted for mitigating the adverse effects of potentially exciting energy sources (e.g., light). For example, the object may be isolated from potentially exciting energy sources. Isolation may include a complete photo, electro, and/or thermal disconnect between the potential source(s) and the object to be protected. Another strategy may include filtering the potential source(s) such that the object and potential source are in limited photo, electro, and/or thermal communication. For example, light may be filtered (e.g., using a sunscreen) such that less or no radiation can reach the object to produce adverse effects in the object. In yet another approach, adverse effects from potentially exciting energy sources may also be mitigated by limiting or preventing free radical damage. For example, anti-oxidants may be added to react with the free radicals formed before the radicals have an opportunity to interact with and damage the object to be protected.

These strategies may not always produce desired results. Accordingly, it may be desirable to move upstream in the excitation process. For example, preventing radical formation may have advantages over applying antioxidants afterwards. Isolation and/or filtering techniques may be employed to prevent formation of the excited energy state. However, these approaches may not be satisfactory either, for example, where exposure of the object to the potentially exciting energy source is desirable, necessary and/or inevitable.

According to some embodiments, the present disclosure relates to molecules, compositions, systems, and methods for promptly resolving excited energy states after formation. Excited state resolution may occur through a pathway or pathways that mitigate or prevent unwanted and/or harmful effects (e.g., radical formation, sensitization of surrounding molecules, producing unwanted photoproducts).

According to some embodiments, compositions, systems, and methods of the present disclosure may be operable without regard to the source of the excitation energy. For example, excited energy states may be resolved where the excited state arose from another excited species by way of sensitization and/or direct electromagnetic radiation of any wavelength sufficient to eject an electron from its ground state to an excited state. Examples of electromagnetic radiation include visible light, ultra violet radiation, and X-rays.

Chemical Entity

In some embodiments, the present disclosure relates to substituted propenoic acid derivatives (amides or thiol esters). For example, a substituted propenoic amide may comprise an aryl substituted propenoic amide. An aryl substituted propenoic amide may have a structure according to Formula I:

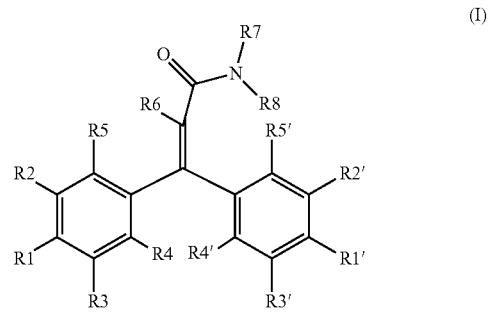

wherein
R1 and R1' are each, independently, is a methoxyl group (—OCH$_3$) or a hydrogen (H) with at least one being a methoxyl group (—OCH$_3$),
R2, R2', R3, R3', R4, R4', R5, R5' are each, independently, selected from H, OH, alkyl, alkoxyl, substituted alkyl group,
R6: is cyano or

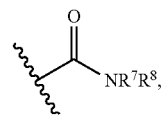

and
R7 and R8 are each, independently, selected from H, alkyl, substituted alkyl (e.g., ether or ester-containing substituted alkyl) and a polymeric structure.

An aryl substituted propenoic acid thiol ester may have a structure according to Formula II:

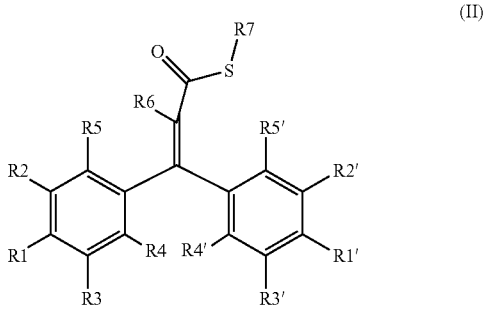

(II)

Wherein

R1 and R1' are each, independently, is a methoxyl group (—OCH₃) or a hydrogen (H) with at least one being a methoxyl group (—OCH₃), R2, R2', R3, R3', R4, R4', R5, R5' are each, independently, selected from H, OH, alkyl, alkoxyl, substituted alkyl group, R6: is cyano or

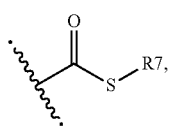

and

R7 is selected from alkyl, substituted alkyl (e.g., ether or ester-containing substituted alkyl) and a polymeric structure.

An aryl substituted propenoic amide/thiol ester is capable of accepting energy effectively from other excited molecules and may be stable according to some embodiments. Excited energy state resolution may occur without observable (e.g., detectable) photochemical reaction derived from the excited state. For example, an aryl substituted propenoic amide/thiol ester may not have any observed photochemical reaction upon interacting with an excited state molecule. An aryl substituted propenoic amide/thiol ester, in some embodiments, may dissipate excited state energy. For example, an aryl substituted propenoic amide/thiol ester may contact a donor molecule having an excited energy state, accept the excited state energy, allowing the donor to assume a lower energy state (e.g., ground state), and subsequently dissipate the excited energy through (e.g., substantially entirely through) one or more non-radiative pathways. For example, an aryl substituted propenoic amide/thiol ester may dissipate excited state energy as kinetic energy and/or heat according to some embodiments.

According to some embodiments, an aryl group may comprise a carbocyclic aromatic ring system having a single ring, two fused rings, or three fused rings. An aryl group may be selected from phenyl, naphthyl, tetrahydronaphthyl, phenanthrenyl, biphenylenyl, indanyl, indenyl, anthracenyl, and fluorenyl.

An alkyl group may comprise, in some embodiments, a straight- and/or branched-chain hydrocarbon having from about 1 to about 30 (C1-C30) or more carbon atoms. Examples of alkyl groups may include methyl, ethyl, n-propyl, isopropyl, n-butyl, sec-butyl (2-methylpropyl), t-butyl (1,1-dimethylethyl), and 3,3-dimethylpentane. An alkoxyl group may comprise —O-alkyl, in some embodiments.

A substituted alkyl group may comprise, in some embodiments, an alkyl having one or more substituents. Substituents may include, for example, heteroalkyl, ester, carboxy, cyano, amino, amido, sulfur, and/or halo. In some embodiments, a substituted alkyl group may be mono-, di-, or tri-substituted at each of one, two, or three carbon atoms. Substituents may be present on a single carbon or distributed among more than one carbons.

According to some embodiments, a polymeric structure may comprise a step-growth polymer such as a polyester, a polyamides, or a polyurethane. The polymer structure can also be a chain-growth polymer such as a polyacrylate, a polystyrene, a polyolefine and their co-polymer.

A cyano group may comprise a —C≡N (also "—CN"), in some embodiments.

In some embodiments, an aryl substituted propenoic amide/thiol ester may require R4 and R4' to be separate (i.e., not fused to each other). An aryl substituted propenoic amide, according to some embodiments, may not include halogen at R2, R2', R3, R3', R4, R4', R5, and/or R5', may not include nitrogen at R2, R2', R3, R3', R4, R4', R5, and/or R5', and/or may not include sulfur at R2, R2', R3, R3', R4, R4', R5, and/or R5'. In some embodiments, an aryl substituted propenoic amide may require R6 to be other than —CN.

According to some embodiments, an aryl substituted propenoic amide/thiol esters may have a molecular weight of less than about 1,500, less than about 1,000, less than about 950, less than about 900, less than about 850, less than about 800, less than about 750, less than about 700, less than about 650, and/or less than about 600. An aryl substituted propenoic amide/thiol ester may require R7 and/or R8 to have a structure other than a polymeric structure, in some embodiments. An aryl substituted propenoic amide/thiol esters, according to some embodiments, may comprise only one aryl substitution on the propenoic amide moiety.

Compositions

The present disclosure relates, in some embodiments, to compositions operable to reduce and/or eliminate unwanted effects of excited energy states. For example, compositions may resolve excited energy states with little or no radical formation, with little or no unwanted photochemical by-products, with little or no undesired radiative processes.

A composition may comprise, in some embodiments, an aryl substituted propenoic amide according to Formula I, an aryl substituted propenoic acid thiol ester according to Formula II, or combinations thereof. A composition may be formulated for use as a paint, a coating, a cosmetic, a sunscreen, a pharmaceutical, or combinations thereof. In some embodiments, an aryl substituted propenoic amide/thiol ester may be included in an extruded composition (e.g., comprising a natural and/or synthetic polymer).

According to some embodiments, the concentration of the aryl substituted propenoic amide/thiol ester may be from about 0.1% to about 30% by weight. It may be desirable to vary the concentration according to the nature of any photoactive materials present, the amount of any photoactive materials present, the wavelength(s) of incident radiation, the intensity of incident radiation, the ambient temperature, and/or the nature of the object to be protected. For example, where the incident radiation is intense and includes wavelength(s) that readily excite photoactive molecules, a higher concentration of aryl substituted propenoic amide may be desired because of the higher frequency of excited state formation that may be anticipated. Higher concentrations may be desirable to enhance protective effect and considerations of toxicity may be attenuated, for example, where the material to be protected is non-living tissue (e.g., materials applications). Lower concentrations of aryl substituted propenoic amide may be desirable, in some embodiments, for compositions that may require inclusion of other components. For example, lower concentrations may allow a formulator to include other materials needed for sensorial purpose etc. Compositions comprising an aryl substituted propenoic amide/thiol ester may be in liquid, solid, or gaseous (e.g., vapor) form.

A composition may include, according to some embodiments, one or more excipients, carriers, additives, fragrances, pigments, solvents, and/or diluents, such as film forming polymers, flow and leveling additives, different colorants, and the like.

According to some embodiments, a composition may comprise a photoactive molecule and an aryl substituted propenoic amide/thiol ester (e.g., according to Formula I & II). The aryl substituted propenoic amide/thiol ester may be positioned within the composition to be in electrical communication with the photoactive molecule(s) in some embodiments. The photoactive molecule may acquire an excited energy state when exposed to radiation. The aryl substituted propenoic amide(s)/thiol esters may accept the excited energy state electron from the photoactive molecule(s) allowing the photoactive molecule(s) to return to a lower energy state (e.g., ground state). The excited substituted propenoic acid derivative may dissipate its acquired energy through one or more non-radiative pathways in some embodiments. A first composition comprising a photoactive molecule alone may display lower photostability than a second composition comprising a photoactive molecule with an aryl substituted propenoic acid derivative (e.g., according to Formula I & II), in some embodiments. A composition comprising a photoactive molecule and an aryl substituted propenoic acid derivative (e.g., according to Formula I & II), according to some embodiments, may display higher photostability than a composition with the same components except lacking an aryl substituted propenoic acid derivatives.

Photostability may be assessed according to any desired metric. In some embodiments, a photoactive compound may be considered stable when, for example, after 30 MED irradiation the photoactive compound has retained at least about 90% of its original absorbance. Similarly, a composition (e.g., with more than one kind of photoactive molecule) may be considered stable, as a whole, when, for example, after 30 MED irradiation the sunscreen composition has retained at least about 90% of its original absorbance. Absorbance may be assessed at a single wavelength and/or over a range of wavelengths of interest (e.g., the wavelength at which a photoactive compound has a peak absorbance). According to some embodiments, photostability assessments use the same absorbance metric (e.g., single wavelength, plurality of wavelengths, continuous range of wavelengths) before and after exposure to 30 MED irradiation. Photostability can also be assessed by monitoring chemical or physical properties changes after exposure to a set irradiation conditions, such as a defined time in an experimental devise simulating sun light or exposure to a period time under direct sunlight.

Devices

The present disclosure relates, in some embodiments, to objects, articles, and/or devices (collectively "objects) comprising an aryl substituted propenoic acid derivatives (Formulation I & II). For example, objects that may be exposed to sunlight may be manufactured to include an aryl substituted propenoic amide/thiol ester. Objects that may be exposed to sunlight include building materials (e.g., a roofing material, a siding material), sporting goods (e.g., netting, balls), fabrics (e.g., clothing, awnings, coverings, sails), vehicle materials (e.g., vehicle coatings, covers, tops, tires, ground effects), medical devices (e.g., a prosthetic, a wheelchair), and others. In some embodiments, an object may comprise an aryl substituted propenoic acid derivatives homogeneously throughout or in selected portions (e.g., only regions that may be exposed to exciting heat and/or irradiation).

Methods of Use

The present disclosure relates, according to some embodiments, to methods for resolving excited energy states substantially without radical formation. A method may comprise positioning an aryl substituted propenoic amide/thiol ester in electrical communication with a photoactive molecule comprising an excited state electron under conditions that permit the aryl substituted propenoic amide to accept the excited state energy or electron. Positioning an aryl substituted propenoic amide/thiol ester may include, for example, contacting an aryl substituted propenoic amide/thiol ester with a photoactive molecule, mixing an aryl substituted propenoic amide/thiol ester and a photoactive molecule together in an electrically conductive media (e.g., liquid media, solid media, gel media, setting media, and the like), electrically connecting an aryl substituted propenoic amide/thiol ester and a photoactive molecule, and/or combinations thereof.

Methods of Making

The present disclosure relates to methods for preparing an aryl substituted propenoic amide, in some embodiments. For example, an aryl substituted propenoic amide may be prepared by a Knoevenagel condensation of a ketone with an active hydrogen-containing structure.

As will be understood by those skilled in the art who have the benefit of the instant disclosure, other equivalent or alternative compositions, objects, methods, and systems for quenching, dissipating, and/or otherwise resolving excited state energy can be envisioned without departing from the description contained herein. Accordingly, the manner of carrying out the disclosure as shown and described is to be construed as illustrative only.

Persons skilled in the art may make various changes in the kind, number, and/or arrangement of R-groups, substituents, and/or heteroatoms without departing from the scope of the instant disclosure. In addition, the size of an object and/or system may be scaled up or down to suit the needs and/or desires of a practitioner. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Persons skilled in the art may make various changes in methods of preparing and using a composition, device, and/or system of the disclosure. For example, a composition, object, and/or system may be prepared and or used as appropriate for animal and/or human use (e.g., with regard to sanitary, infectivity, safety, toxicity, biometric, and other considerations). Elements, compositions, objects, systems, methods, and method steps not recited may be included or excluded as desired or required.

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value+/- about 10%, depicted value+/- about 50%, depicted value+/- about 100%) and/or a range endpoint. With respect to the former, a value of 50 depicted in an example, table, and/or drawing may form the basis of a range of, for example, about 45 to about 55, about 25 to about 100, and/or about 0 to about 100. Disclosed percentages are weight percentages except where indicated otherwise.

All or a portion of an object and/or system for quenching, dissipating, and/or otherwise resolving excited state energy may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

The title, abstract, background, and headings are provided in compliance with regulations and/or for the convenience of the reader. They include no admissions as to the scope and content of prior art and no limitations applicable to all disclosed embodiments.

EXAMPLES

Some specific embodiments of the disclosure may be illustrated by one or more of the examples provided herein.

Example 1

General Procedure for the Preparation of Thiol Esters

1-Decanethiol (1.2 equiv) and 4-Dimethylaminopyridine (0.05 equiv) were added to a solution of the 3-(4-Methoxyphenyl)-3-phenyl-2-cyano-2-propenoic acid in dry methylene chloride (2 mL/mmol) at room temperature followed by 1-Ethyl-3-(3-dimethylaminopropyl)carbodiimide (EDC, 1.5 equiv). The mixture was stirred for 12 h at room temperature. At the end of the reaction the organic phase was washed with water, brine and dried over MgSO$_4$, filtered, and concentrated in vacuo. The crude product was purified by flash chromatography (silica gel, ethyl acetate in hexanes) affording the desired product as yellow oil (65%).

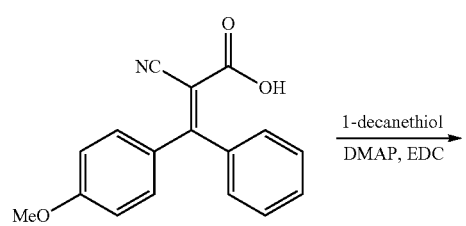

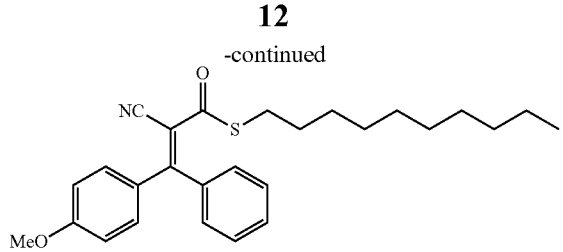

Example 2

General Procedure for the Preparation of Amides

Hexylamine (1.1 equiv) was added to methyl methoxyl crylene in a round bottom flask at room temperature. The mixture was stirred for 8 h at 130° C. under nitrogen atmosphere. At the end of the reaction the mixture was cooled to room temperature and then dissolved in ethyl acetate. The organic solution was washed with 1N HCl, water, brine and dried over MgSO$_4$, filtered, and concentrated in vacuo. The crude product was purified by flash chromatography (silica gel, ethyl acetate in hexanes) affording the desired product as light yellow oil (70%).

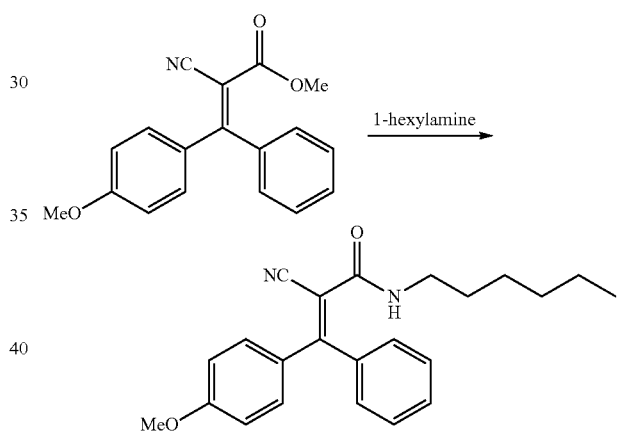

What is claimed is:

1. A composition comprising:
a photoactive molecule; and
a substituted propenoic amide,
wherein the propenoic amide has a structure according to Formula I:

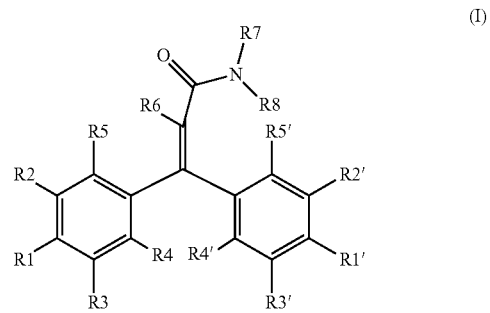

wherein R1 and R1' are each, independently, a methoxyl group (—OCH$_3$) or a hydrogen (H) with at least one being a methoxyl group (—OCH$_3$), R2, R2', R3, R3', R4, R4', R5, R5' are each, independently, H, OH, alkyl, alkoxyl, or a substituted alkyl group, R6: is cyano or

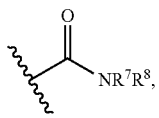

and

R7 and R8 are each, independently, H, alkyl, substituted alkyl or a polymeric structure, and wherein the aryl substituted propenoic amide is configured (a) to resolve at least one excited state of the photoactive molecule without observable photochemical reaction, (b) to resolve at least one excited state of the photoactive molecule non-radiatively, or (c) to resolve at least one excited state of the photoactive molecule without observable photochemical reaction and non-radiatively;

wherein the alkyl group may be selected from methyl, ethyl, n-propyl, isopropyl, n-butyl, sec-butyl (2-methylpropyl), t-butyl (1,1-dimethylethyl), and 3,3-dimethylpentane, straight chain hydrocarbon having from about 1 to about 30 (C1-C30) or more carbon atoms, or branched-chain hydrocarbon having from about 1 to about 30 (C1-C30) or more carbon atoms;

wherein the polymeric structure may be selected from polyester, polyamide, polyurethane, polyacrylate, polystyrene, polyolefin, or any copolymer thereof;

wherein the substituted alkyl group may have one or more substituents selected from heteroalkyl, ester, ether, carboxy, cyano, amino, amido, sulfur, halo, or any combination thereof.

2. A composition according to claim 1, wherein R1 is hydrogen and R1' is a methoxyl group (—OCH$_3$).

3. A composition according to claim 1, wherein R1 is a methoxyl group (—OCH$_3$) and R1' is hydrogen.

4. A composition according to claim 1, wherein at least one of R2, R2', R3, R3', R4, R4', R5, and R5' is an alkyl group having from about 1 to about 30 carbon atoms.

5. A composition according to claim 1, wherein at least one of R2, R2', R3, R3', R4, R4', R5, and R5' is alkoxyl.

6. A composition according to claim 1, wherein at least one of R2, R2', R3, R3', R4, R4', R5, and R5' is a substituted alkyl group;

wherein the substituted alkyl group may have one or more substituents selected from heteroalkyl, ester, ether, carboxy, cyano, amino, amido, sulfur, halo, or any combination thereof.

7. A composition according to claim 1, wherein R6 is

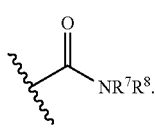

8. A paint, a coating, a cosmetic, a sunscreen, or a pharmaceutical comprising a composition according to claim 1.

9. A substituted propenoic amide having a structure according to Formula I:

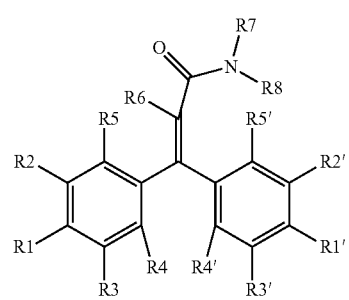

wherein

R1 and R1' are each, independently, a methoxyl group (—OCH$_3$) or a hydrogen (H) with at least one being a methoxyl group (—OCH$_3$), R2, R2', R3, R3', R4, R4', R5, R5' are each, independently, H, OH, alkyl, alkoxyl, or a substituted alkyl group, R6: is cyano or

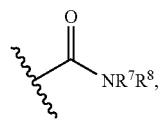

and

R7 and R8 are each, independently, H, alkyl, substituted alkyl or a polymeric structure, and wherein the aryl substituted propenoic amide is configured (a) to resolve at least one excited state of a photoactive molecule without observable photochemical reaction, (b) to resolve at least one excited state of a photoactive molecule non-radiatively, or (c) to resolve at least one excited state of a photoactive molecule without observable photochemical reaction and non-radiatively;

wherein the alkyl group may be selected from methyl, ethyl, n-propyl, isopropyl, n-butyl, sec-butyl (2-methylpropyl), t-butyl (1,1-dimethylethyl), and 3,3-dimethylpentane, straight chain hydrocarbon having from about 1 to about 30 (C1-C30) or more carbon atoms, or branched-chain hydrocarbon having from about 1 to about 30 (C1-C30) or more carbon atoms;

wherein the polymeric structure may be selected from polyester, polyamide, polyurethane, polyacrylate, polystyrene, polyolefin, or any copolymer thereof;

wherein the substituted alkyl group may have one or more substituents selected from heteroalkyl, ester, ether, carboxy, cyano, amino, amido, sulfur, halo, or any combination thereof.

10. A substituted propenoic amide according to claim 9, wherein R1 is hydrogen and R1' is a methoxyl group (—OCH$_3$).

11. A substituted propenoic amide according to claim 9, wherein R1 is a methoxyl group (—OCH$_3$) and R1' is hydrogen.

12. A substituted propenoic amide according to claim 9, wherein at least one of R2, R2', R3, R3', R4, R4', R5, and R5' is an alkyl group having from about 1 to about 30 carbon atoms.

13. A substituted propenoic amide according to claim 9, wherein at least one of R2, R2', R3, R3', R4, R4', R5, and R5' is alkoxyl.

14. A substituted propenoic amide according to claim 9, wherein at least one of R2, R2', R3, R3', R4, R4', R5, and R5' is a substituted alkyl group;
wherein the substituted alkyl group may have one or more substituents selected from heteroalkyl, ester, ether, carboxy, cyano, amino, amido, sulfur, halo, or any combination thereof.

15. A substituted propenoic amide according to claim 9, wherein R6 is

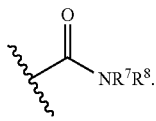

16. A paint, a coating, a cosmetic, a sunscreen, or a pharmaceutical comprising a substituted propenoic amide according to claim 9.

17. A method for resolving at least one excited energy state of a photoactive molecule, the method comprising:
positioning the photoactive molecule in electrical communication with a substituted propenoic amide prior to, during, or following excitation of the photoactive molecule to the at least one excited energy state,
wherein the substituted propenoic amide has a structure according to Formula I:

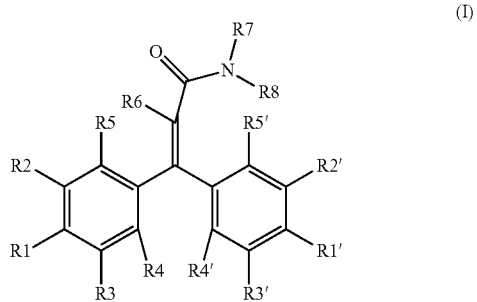

(I)

Wherein
R1 and R1' are each, independently, a methoxyl group (—OCH$_3$) or a hydrogen (H) with at least one being a methoxyl group (—OCH$_3$),
R2, R2', R3, R3', R4, R4', R5, R5' are each, independently, H, OH, alkyl, alkoxyl, or a substituted alkyl group,
R6: is cyano or

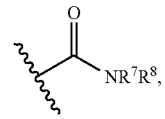

and
R7 and R8 are each, independently, H, alkyl, substituted alkyl or a polymeric structure;
wherein the alkyl group may be selected from methyl, ethyl, n-propyl, isopropyl, n-butyl, sec-butyl (2-methylpropyl), t-butyl (1,1-dimethylethyl), and 3,3-dimethylpentane, straight chain hydrocarbon having from about 1 to about 30 (C1-C30) or more carbon atoms, or branched-chain hydrocarbon having from about 1 to about 30 (C1-C30) or more carbon atoms;
wherein the polymeric structure may be selected from polyester, polyamide, polyurethane, polyacrylate, polystyrene, polyolefin, or any copolymer thereof;
wherein the substituted alkyl group may have one or more substituents selected from heteroalkyl, ester, ether, carboxy, cyano, amino, amido, sulfur, halo, or any combination thereof.

18. A method according to claim 17, wherein the at least one excited state of the photoactive molecule is resolved without observable photochemical reaction.

19. A method according to claim 17, wherein the at least one excited state of the photoactive molecule is resolved non-radiatively.

20. A method according to claim 17, wherein the at least one excited state of the photoactive molecule is resolved without observable photochemical reaction and non-radiatively.

* * * * *